(12) United States Patent
Roy et al.

(10) Patent No.: US 11,344,706 B2
(45) Date of Patent: May 31, 2022

(54) APPARATUS FOR SECURING MEDICAL DRAIN TUBE

(71) Applicant: Neil Roy LLC, Bethesda, MD (US)

(72) Inventors: Neil Roy, Bethesda, MD (US); Sam Suchin, Pikesville, MD (US)

(73) Assignee: Neil Roy LLC, Bethesda, MD (US)

( * ) Notice: Subject to any disclaimer, the term of this patent is extended or adjusted under 35 U.S.C. 154(b) by 169 days.

(21) Appl. No.: 16/865,038

(22) Filed: May 1, 2020

(65) Prior Publication Data
US 2021/0338989 A1    Nov. 4, 2021

(51) Int. Cl.
*A61M 27/00* (2006.01)
*B65D 63/10* (2006.01)
*B65D 63/00* (2006.01)

(52) U.S. Cl.
CPC ............. *A61M 27/00* (2013.01); *B65D 63/00* (2013.01); *B65D 63/109* (2013.01); *B65D 63/1018* (2013.01); *B65D 63/1081* (2013.01); *A61M 2209/088* (2013.01); *A61M 2210/101* (2013.01)

(58) Field of Classification Search
CPC ............ B65D 63/1018; B65D 63/1081; B65D 63/109; B65D 63/00; Y10Y 24/1498
See application file for complete search history.

(56) References Cited

U.S. PATENT DOCUMENTS

| | | | |
|---|---|---|---|
| 3,009,220 A | 11/1961 | Fein | |
| 4,866,816 A * | 9/1989 | Caveney | F16L 3/233 24/16 PB |
| 5,154,376 A * | 10/1992 | Baum | F16L 3/2332 24/16 PB |
| 5,644,819 A * | 7/1997 | Lyons | B65D 63/08 24/20 R |
| 5,836,053 A * | 11/1998 | Davignon | F16L 3/233 24/16 PB |
| 10,004,536 B2 * | 6/2018 | Hoglund | A61B 17/12009 |

OTHER PUBLICATIONS

L. Santhosh et al., "Chest Tube Complications", PSNet Patient Safety Network, Jun. 2017, p. 1-6, Agency for Healthcare Research and Quality.

* cited by examiner

*Primary Examiner* — Robert Sandy
*Assistant Examiner* — Louis A Mercado
(74) *Attorney, Agent, or Firm* — Intrinsic Law Corp.

(57) ABSTRACT

A device for releasably and adjustably securing a medical tube includes a receiver and a tail, which may be used for thoracostomy. The receiver has a receiver aperture and receiver teeth. The tail has center holes along a central axis of the device. Raised tail teeth are formed on the tail between the central axis and the tail sides. The tail teeth are arranged to engage the receiver teeth when an end of the tail is fed through the receiver aperture to form a tail loop. The receiver teeth define receiver teeth apertures that are smaller than the receiver aperture. The tail loop is adjustable to tighten around the medical tube.

20 Claims, 8 Drawing Sheets

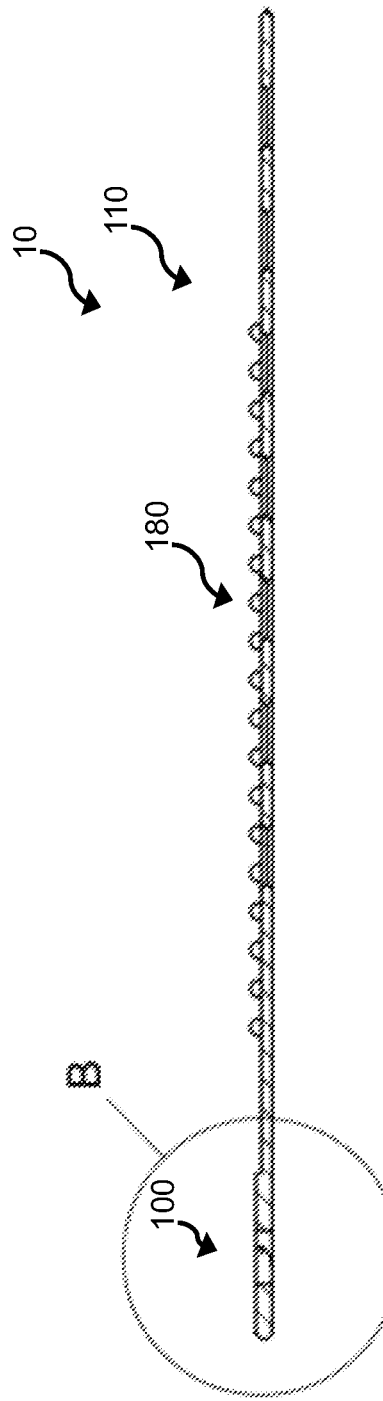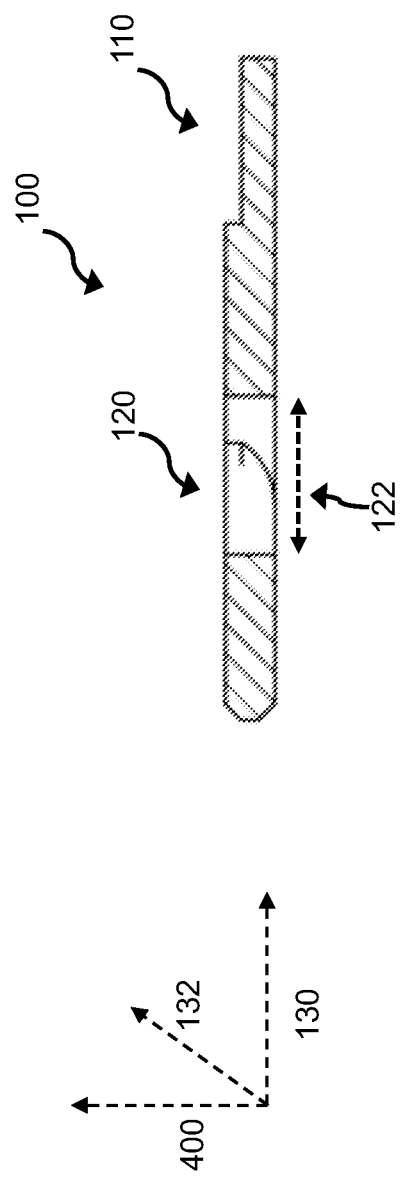
FIG. 4A
FIG. 4B

APPARATUS FOR SECURING MEDICAL DRAIN TUBE

TECHNICAL FIELD

This application generally relates to medical tubing and drainage systems including those used in thoracostomy procedures.

BACKGROUND

Some medical procedures require intubating a patient using a flexible tube, which can be used for drainage of fluids from a location within the patient's body to outside the patient's body, or a thoracostomy. Patients with collapsed lungs (pneumothorax), fluid outside the lung (pleural effusion, hemothorax), pulmonary ailments and emergencies, and other conditions may experience a dangerous fluid or air buildup in volumes within the body that should not sustain such buildup. A thoracostomy is a surgical procedure in which access is gained to the patient's thoracic cavity. A medical tube may be employed during a thoracotomy to drain or suction unwanted fluids from the patient's body.

It is challenging to secure a medical drain tube relative to a patient. The conventional approach is to form a surgical thread loop around the medical drain tube and pass one end of the surgical thread through the patient's skin, such as through the skin on the patient's chest. However, the surgical thread must be tied quickly around the tube so that the patient does not move, thereby moving the tube, and it must be tied tightly so that the tube does not move once tied. Therefore, the process of using suture thread to secure a medical drain tube may lead to several complications that potentially can be life threatening.

While obtaining the suture material and during suturing, the tube may advance into the body further, leading to damage to internal structures, or it may dislodge entirely, leading to life-threatening bleeding and loss of the tube/tract path. During the process of suturing the tube, the tube may become dislodged as the physician must use both hands to suture the tube. In addition, the suture thread may tear, which requires the provider to re-start the procedure. Suture thread is not antibiotic-impregnated or sterile and may lead to ascending infections into the chest cavity. Lastly, it is difficult for the provider to place the tube in the patient at the appropriate depth because the tube is not marked.

It would be desirable to overcome these and/or other deficiencies in the art.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a device comprising: a receiver having a receiver body that defines a receiver aperture having a receiver aperture length that is measured with respect to a central axis of the device, the receiver body having a receiver tooth that extends into the receiver aperture to define a receiver tooth aperture having a receiver tooth aperture length that is measured with respect to the central axis, the receiver tooth aperture length narrower than the receiver aperture length; and a tail extending from the receiver along the central axis to a tail end, the tail defining a plurality of center holes and a plurality of tail teeth, the tail teeth axially aligned with the receiver tooth. The device is releasably configurable between a disengaged state and an engaged state. In the engaged state, the tail end is passed through the receiver aperture such that the tail forms a loop to secure an object, and the receiver tooth mechanically engages a first tail tooth to releasably secure the tail in the loop. In the disengaged state, the receiver tooth and the one of the tail teeth are mechanically disengaged and the tail end is removed from the receiver aperture.

In one or more embodiments, the tail teeth form a row that is axially aligned with the receiver tooth. In one or more embodiments, the tail teeth are evenly spaced along a length of the tail, the length of the tail measured with respect to the central axis. In one or more embodiments, the center holes form a row that is axially aligned with the receiver aperture where the receiver aperture has the receiver aperture length. In one or more embodiments, the center holes are evenly spaced along a length of the tail, the length of the tail measured with respect to the central axis. In one or more embodiments, the center holes form a first row and the tail teeth form a second row, the first and second rows parallel to the central axis.

In one or more embodiments, the receiver tooth comprises a first receiver tooth that defines a first receiver tooth aperture having a first receiver tooth aperture length, and the receiver body has a second receiver tooth that extends into the receiver aperture to define a second receiver tooth aperture having a second receiver tooth aperture length. In one or more embodiments, the first receiver tooth aperture length is about the same as the second receiver tooth aperture length. In one or more embodiments, the receiver aperture has the receiver aperture length in a middle region of the receiver aperture, and the first and second receiver teeth are disposed on opposing sides of the middle region of the receiver aperture.

In one or more embodiments, the device further comprises an ear attached to the receiver, the ear having an ear body that defines an ear aperture. In one or more embodiments, the ear is laterally offset from the central axis along a lateral axis, the lateral axis orthogonal to the central axis. In one or more embodiments, the ear comprises a first ear that has a first ear body that defines a first ear aperture, and the device further comprises a second ear having a second ear body that defines a second ear aperture. In one or more embodiments, the first and second ears are laterally offset from the central axis along a lateral axis, the lateral axis orthogonal to the central axis. In one or more embodiments, the first and second ears are attached to opposing sides of the receiver. In one or more embodiments, the first and second ears are foldably attached to the opposing sides of the receiver In one or more embodiments, the receiver and the tail comprise a monolithic structure In one or more embodiments, the center holes are configured to receive surgical thread. In one or more embodiments, in the engaged state a diameter of the loop can be increased by mechanically engaging the receiver tooth with a second tail tooth, the second tail tooth disposed closer to the tail end than the first tail tooth. In one or more embodiments, in the engaged state a diameter of the loop can be decreased by mechanically engaging the receiver tooth with a second tail tooth, the first tail tooth disposed closer to the tail end than the second tail tooth. In one or more embodiments, in the engaged stated the loop is configured to secure a medical tube. In one or more embodiments, the device further comprises an adhesive disposed on the tail.

BRIEF DESCRIPTION OF THE DRAWINGS

For a fuller understanding of the nature and advantages of the present concepts, reference is made to the following detailed description of preferred embodiments in connection with the accompanying drawings.

FIGS. 4A and 4B are cross-sectional views of the device illustrated in FIG. 1.

DETAILED DESCRIPTION

Figure 1:
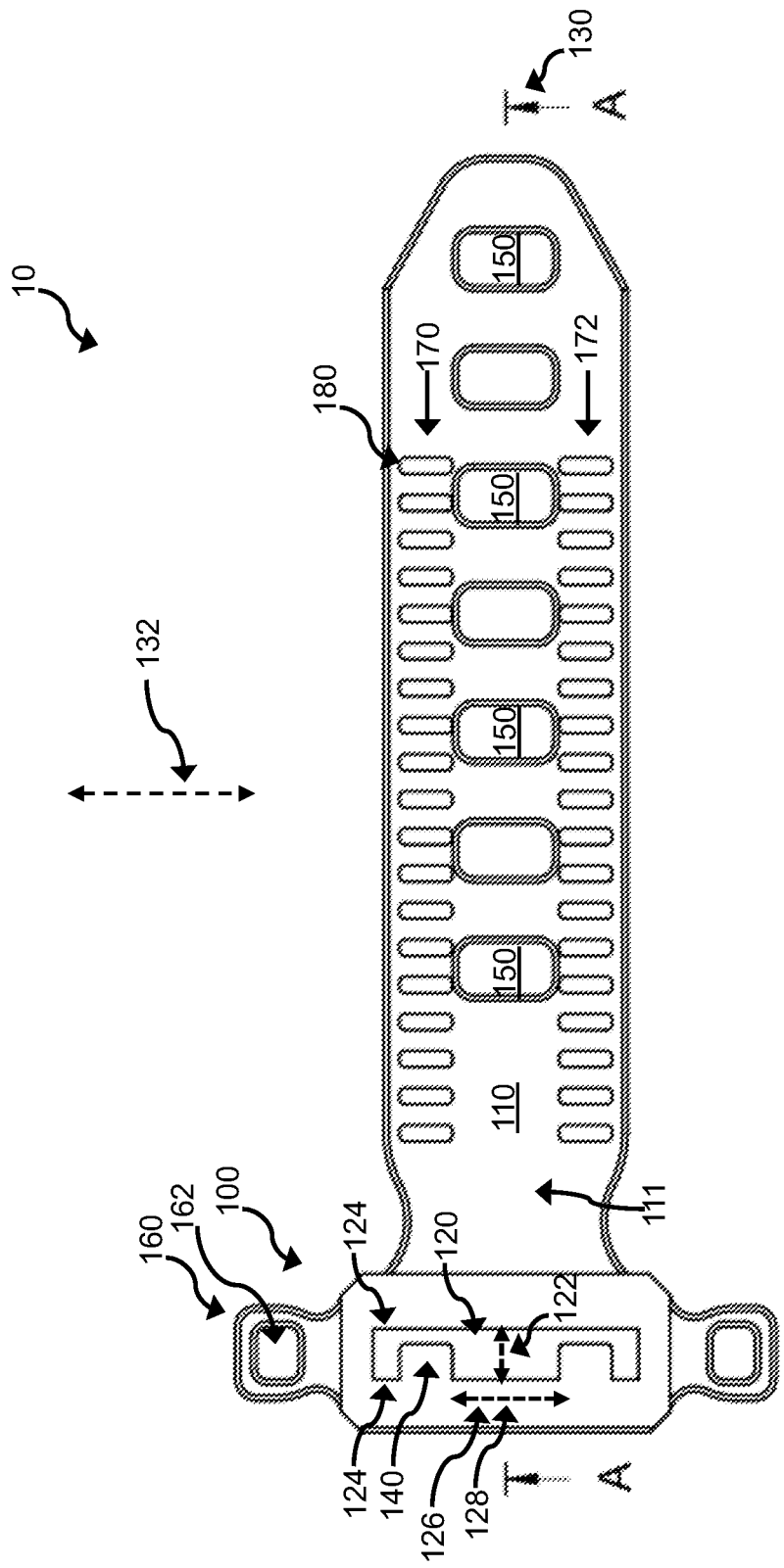
FIG. 1 is a top view of a device 10 for releasably and adjustably securing a medical tube in a first or disengaged state according to an embodiment.

A device for releasably and adjustably securing a medical thoracostomy tube is disclosed. The device includes a receiver and a tail that extends from the receiver. The receiver has a receiver body that defines a receiver aperture having a receiver aperture length. One or more receiver teeth extend into the receiver aperture to define a corresponding one or more receiver teeth aperture(s) (in general, receiver teeth apertures). The receiver teeth apertures have a receiver tooth aperture length that is smaller or narrower than the receiver aperture length.

The tail has a tail body that is elongated and extends from the receiver along a central axis of the device. Center holes are defined in the tail body and extend along the central axis such that the central axis passes through each center hole. Tail teeth are formed on the tail body between the central axis and a side of the tail body, the side having a length that is parallel to the central axis. The tail teeth are raised with respect to a planar surface of the tail body. The tail teeth are arranged to mechanically engage the receiver teeth when a tail end of the tail is passed through the receiver aperture to releasably and adjustably secure the tail in a loop.

The diameter of the loop can be decreased by pulling the tail end so that a closer neighboring tail tooth engages the receiver tooth instead of the current tail tooth, the closer neighboring tail tooth disposed closer to the tail end than the current tail tooth. The diameter of the loop can be increased by pulling the loop so that a further neighboring tail tooth engages the receiver tooth instead of the current tail tooth, the further neighboring tail tooth disposed further away from the tail end than the current tail tooth.

In a preferred embodiment, the tail teeth are arranged in two rows with the center holes disposed between each row of tail teeth. Each row of tail teeth is configured and arranged to mechanically engage a corresponding receiver tooth when the tail end of the tail is passed through the receiver aperture. The tail teeth in each row are preferably aligned and equally spaced so that a corresponding tail tooth in each row mechanically engages a corresponding receiver tooth at the same time.

A first ear can be foldably attached to a first edge of the receiver, the first edge disposed laterally from the central axis, which preferably passes through the center of the receiver. The first ear defines a first ear aperture. A second ear can be foldably attached to a second edge of the receiver, the second edge disposed laterally from the central axis and on an opposing side of the receiver. The second ear defines a second ear aperture. The first ear can be used if a physician would like to easily suture the tube to the patient's body.

The loop formed by the tail can be used to secure a medical tube (e.g., a medical thoracostomy tube) or other object. The loop can be tightened to secure the medical tube during a medical procedure and can be loosened at the end of the medical procedure, or as desired. The center holes are preferably used to secure the device to a patient, such as to the patient's skin, using surgical thread or another attachment means. The ear apertures are preferably used to secure the device to the medical tube. In other embodiments, the center holes can be used to secure the device to the medical tube, or to secure the device to both the patient and to the medical tube. Likewise, in other embodiments, the ear apertures can be used to secure the device to the patient, or to secure the device to both the patient and to the medical tube.

Figure 2:
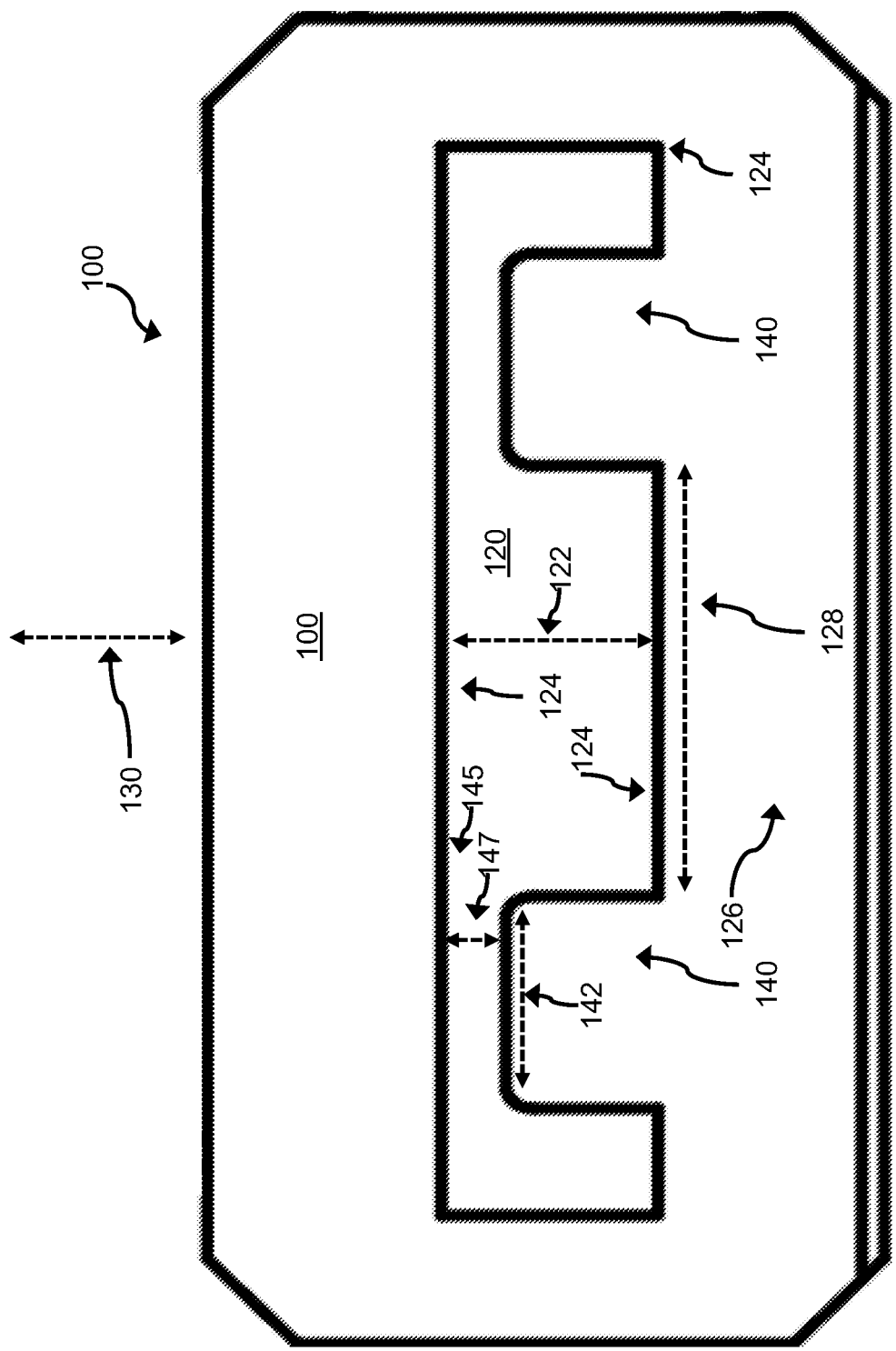
FIG. 2 is an enlarged view of the receiver illustrated in FIG. 1.
Figure 3:
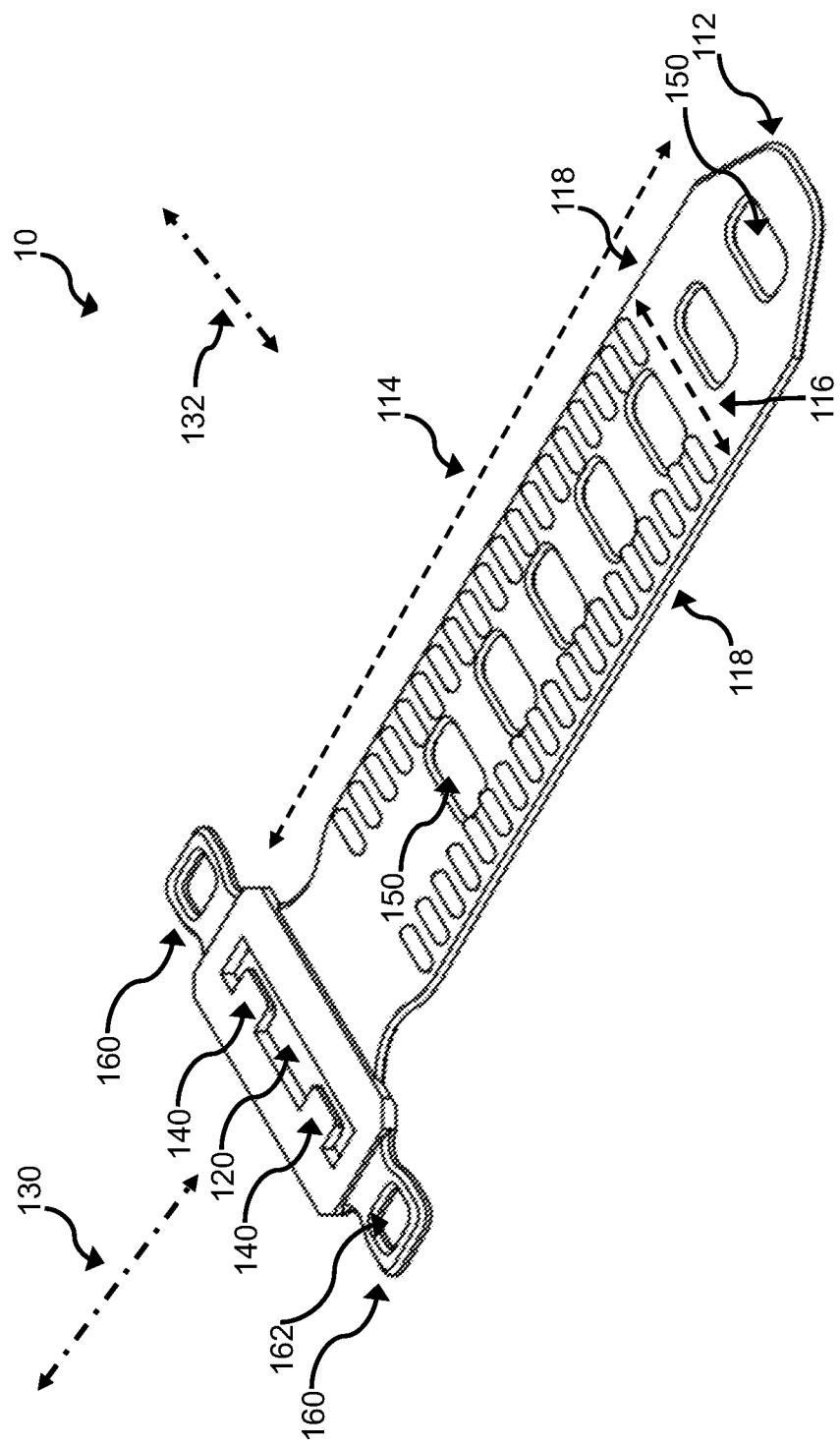
FIG. 3 is a perspective view of the device illustrated in FIG. 1.

FIG. 1 is a top view of a device 10 for releasably and adjustably securing a medical tube (e.g., a medical thoracostomy tube) in a first or disengaged state according to an embodiment. The device 10 includes a receiver 100 and a tail 110 that extends from the receiver 100. FIG. 2 is an enlarged view of the receiver 100, rotated 90 degrees, to further illustrate certain features of the receiver 100. FIG. 3 is a perspective view of the device 10.

The receiver 100 includes a receiver body that defines a receiver aperture 120 having a receiver aperture length 122. The receiver aperture length 122 is measured along a direction that is parallel to a central axis 130 of the device 10. The central axis 130 is coaxial with line A-A in FIG. 1. The receiver aperture length 122 can be measured between opposing inner edges 124 on the perimeter of the receiver aperture 120. The inner edges 124 can extend in a direction that is parallel to a lateral axis 132 which is orthogonal to the central axis 130.

The receiver aperture 120 has the receiver aperture length 122 at least in a middle region 126 of the receiver aperture 120. The central axis 130 passes through the middle region 126. In a preferred embodiment, the middle region 126 is axially symmetric with respect to the central axis 130. The middle region 126 has a width 128 that is measured along a direction that is parallel to the lateral axis 132.

The body of the receiver 100 includes two receiver teeth 140 that extend into the receiver aperture 120 to define tooth apertures 150. Additional or fewer receiver teeth 140 can be provided in other embodiments. Each tooth aperture 145 has a tooth aperture length 147 that is measured along a direction that is parallel to the central axis 130. The tooth aperture length 147 is smaller or narrower than the receiver aperture length 122. Each receiver tooth 140 preferably defines the same tooth aperture length 147. In addition, each receiver tooth 140 has a width 142 that is measured with respect to the lateral axis 132. The width 142 of each receiver tooth 140 defines the width of the corresponding tooth aperture 145. In some embodiments, each receiver tooth 140 is identical.

The receiver teeth 140 are disposed on each side of the middle region 126 of the receiver aperture 120 to define the width 128 of the middle region 126. For example, the distance between the receiver teeth 140 determines the width 128 of the middle region 126. In some embodiments, the receiver 100, the receiver aperture 120, and/or the receiver teeth 140 is/are axially symmetric with respect to the central axis 130. The receiver teeth 140 can extend from the same or different inner edge(s) 124 of the receiver aperture 120.

First and second ears 160 are foldably attached to the top and bottom, respectively, of the receiver 100. The ears 160 are laterally offset from the receiver aperture 120 with respect to the central axis 130. Each ear 160 has a body that defines an ear aperture 162. Each ear aperture 162 is sized to receive surgical thread or another attachment means to attach the corresponding ear 160 to an object, such as a patient, an article of clothing, a medical tube (e.g., an intubation or thoracostomy tube or another medical tube), or another object.

The ears 160 are foldably attached to the receiver 100 which can allow a user (e.g., a surgeon) to adjust the relative orientation of the ears 160 (e.g., by bending and/or pivoting the ears 160) with respect to the receiver 100 and/or with respect to the object to which the ears 160 are to be attached. Adjusting the relative orientation of the ears 160 can allow the user to attach the ears 160 to an object that is curved or bent, such as a curved or bent medical tube, a curved or bent article of clothing, or another object that is curved, bent, or another shape. For example, the user can bend and/or pivot the ears 160 to adjust their relative position with respect to an object for attaching the ears 160 thereto. Additionally or alternatively, adjusting the relative orientation of the ears 160 can improve the user's access to the ears 160 and respective ear apertures 162, such as when inserting surgical thread through the ear apertures 162.

The tail 110 is mechanically coupled to the receiver 100. In some embodiments, the tail 110 and the receiver 100 are integrally formed from a body that is comprised of a single piece of material (e.g., a monolithic structure). Examples of the materials used to form the device 10 include nylon (e.g., nylon 6/6) and/or plastic (e.g., HPDE, high density polyethylene (commonly abbreviated as HDPE), acrylonitrile butadiene styrene (commonly abbreviated as ABD), unplasticized polyvinyl chloride (commonly abbreviated as uPVC), and/or chlorinated polyvinyl chloride (commonly abbreviated as CVPC)).

The tail 110 has a length 114 that extends from the receiver 100 to a tail end 112 along the central axis 130. In addition, the tail 110 has a length 116 that extends across opposing sides 118 of the tail 110 along an axis that is parallel to the lateral axis 132. The tail 110 is elongated such that its length 114 is greater than its width 116. Various dimensions of the length 114 and width 116, and ratios thereof, can be used depending on the intended purpose of the device 10. In addition, the tail 110 is flexible and/or bendable such that the tail end 112 can bend towards and can be inserted into the receiver aperture 120, as illustrated in FIGS. 5-8.

In some embodiments, an adhesive can be disposed to at least a portion of one or both sides 118, which can be used to attach the side 118 of the device 10 to the patient or to another object. The adhesive can also be disposed to the side 118 of the tail 110 at the tail end 112. Additionally or alternatively, the adhesive can be disposed on another portion of the tail 110 and/or on the receiver 100. In some embodiments, some or all of the device 110 can be formed with an antibiotic-impregnated material which can reduce the likelihood of infection to the patient during use. For example, the receiver 100 and at least the portion of the tail 110 can be formed with the antibiotic-impregnated material.

The adhesive can preferably be used to secure the device 10 to the patient. In some embodiments, the device 10 can be secured to the patient only using the adhesive. In other embodiments, the adhesive can be used to temporarily secure the device 10 to patient (e.g., to prevent relative movement between the device 10 and patient) while the physician ties the device 10 to the patient (or other object) and/or to the medical tube (e.g., using surgical thread). Using the adhesive can prevent the device 10 from moving relative to the patient before the device 10 is secured using surgical thread. In some embodiments, the device 10 can be secured to the medical tube before the surgical procedure begins.

A plurality of center holes 150 is defined along the central axis 130 in a middle or center region 111 of the tail 110. The central axis 130 can pass through at least a portion of each center hole 150. In a preferred embodiment, the central axis 130 passes through the center or middle of each center hole 150. Each center hole 150 can be symmetric with respect to the central axis 130 and/or with respect to an axis that is parallel to the lateral axis 132. The center holes 150 are preferably evenly-spaced along the central axis 130. For example, the distance between the center or middle of adjacent center holes 150 can the same. The center holes 150 are axially aligned with respect to the middle region 126 of the receiver aperture 120 where the receiver aperture 120 has the receiver aperture length 122. In a preferred embodiment, the central axis 130 passes through the center or middle of each center hole 150 and through the center or middle of the middle region 126 where the receiver aperture 120 has the receiver aperture length 122.

The center holes 150 are sized to receive surgical thread or another attachment means to attach the tail 110 to an object, such as a patient, an article of clothing, a medical tube (e.g., an intubation tube, thoracostomy tube or another medical tube), or another object. For example, the surgical thread can be threaded in a loop through adjacent center holes 150.

First and second rows 170, 172 of tail teeth 180 are disposed on the tail 110. Each row 170, 172 is parallel to the central axis 130. The tail teeth 180 in each row 170, 172 are sized and arranged to securely and releasably engage a corresponding receiver tooth 140. For example, the tail teeth 180 in the first row 172 are sized to securely and releasably engage a first receiver tooth. Likewise, the tail teeth 180 in the second row 172 are sized and arranged to securely and releasably engage a second receiver tooth.

The tail teeth 180 have a length that is measured with respect to the lateral axis 132. The length of the tail teeth 180 in each row can be about the same as the length of the receiver tooth 140 that corresponds to that row. Thus, the length of the tail teeth 180 can be about the same as the length of the receiver tooth 140 and the corresponding tooth aperture 145. As used herein, "about" means plus or minus 10% of the relevant value.

The tail teeth 180 have a height or thickness that is measured with respect to a vertical axis that is orthogonal to the central axis 130 and the lateral axis 132. The height of each tail tooth 180 is greater than or equal to the tooth aperture length 147 such that the tail teeth 180 engage the receiver teeth 140 when the tail end 112 is inserted through the receiver aperture 120.

The tail teeth 180 in each row are preferably vertically aligned with respect to an axis that is parallel to the lateral axis 132 so that when a tail tooth 180 in the first row 170 engages the first tooth, a corresponding tail tooth 180 in the second row 172 engages the second tooth, and vice versa. Accordingly, the distance between adjacent tail teeth 180 in each row is preferably the same. The distance between adjacent tail teeth 180 can be smaller than the distance between adjacent center holes 150. In some embodiments, the distance between adjacent tail teeth 180 in a row is approximately equal to the thickness of the receiver tooth 140 that corresponds to that row. The thickness of the receiver tooth 140 is measured with respect to a vertical axis that is orthogonal to the central axis 130 and the lateral axis 132.

The dimensions of each tail tooth 180 can be smaller than the corresponding dimensions of each center hole 150. For example, the length of each tail tooth 180 can be smaller than the length of each center hole 150, where the length of the tail teeth 180 and the length of the center holes 150 are measured with respect to the central axis 130. Likewise, the width of each tail tooth 180 can be smaller than the width of each center hole 150, where the width of the tail teeth 180 and the width of the center holes 150 are measured with respect to the lateral axis 132.

The width of the tail end 112, as measured with respect to the lateral axis 132, is preferably tapered, as illustrated in FIGS. 1 and 3, which can facilitate inserting the tail end 112 through the receiver aperture 120. In other embodiments, the tail end 112 is not tapered.

The device 10 is shown in a first or disengaged state in FIG. 1. In this state, the tail end 112 is not passed through the receiver aperture 120. In one example of the first or disengaged state, the device 10 (e.g., the receiver 100 and/or the tail 110) can lay flat when placed on a planar working surface, such as a table. In this example, the tail end 112 and the receiver aperture 120 are located at opposing ends of the device 10.

FIG. 4A. is a cross-section view of device 10 through line A-A in FIG. 1. FIG. 4B is an enlargement of section B of the cross section illustrated in FIG. 4A. As illustrated in FIGS. 4A and 4B, the receiver 100 has a greater cross-sectional thickness than the tail 110. For example, the receiver 100 can have a cross-sectional thickness of about 1 mm to about 5 mm, depending on the size of the medical tube and the material(s) selected for the device 10. FIG. 4A also illustrates that the tail teeth 180 have a height or thickness as measured from the planar surface of the tail 110 with respect to a vertical axis 400. The height or thickness of the tail teeth 180 can be the same or about the same as the receiver tooth aperture length 147. The vertical axis 400 is orthogonal to the central axis 130 and the lateral axis 132. The center holes 150 are also viewable in FIG. 4A.

Figure 5:
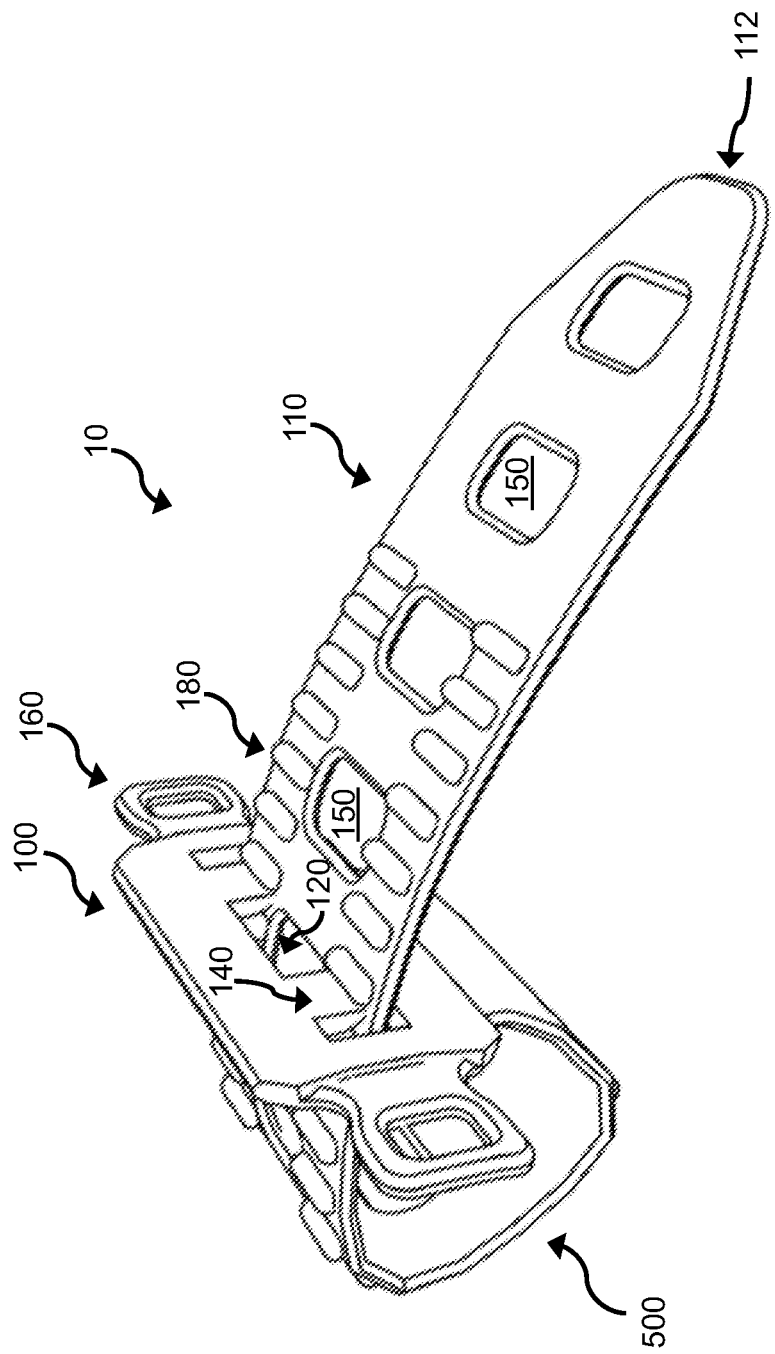
FIG. 5 is a perspective view of the device illustrated in FIG. 1 in a second or engaged state.

FIG. 5 is a perspective view of the device 10 in a second or engaged state in which the tail end 112 is passed through the receiver aperture 120 so that the tail 110 forms a loop 500 to adjustably secure a medical tube (e.g., an intubation or thoracostomy tube). The diameter or size of the loop 500 is adjustable based on the length of the tail 110 that is passed through the receiver aperture 120. The diameter of size of the loop 500 can also be releasably secured by engaging the receiver teeth 140 with the tail teeth 180. The receiver teeth 140 are preferably flexible to allow the receiver teeth 140 to flex towards the tail end 112 as the receiver teeth 140 pass over the tail teeth 180 when the loop 500 is tightened onto the medical tube. Similarly, the receiver teeth 140 can flex away from the tail end 112 as the receiver teeth 140 pass over the tail teeth 180 when the loop 500 is loosened from the medical tube at the end of the medical procedure.

Figure 6:
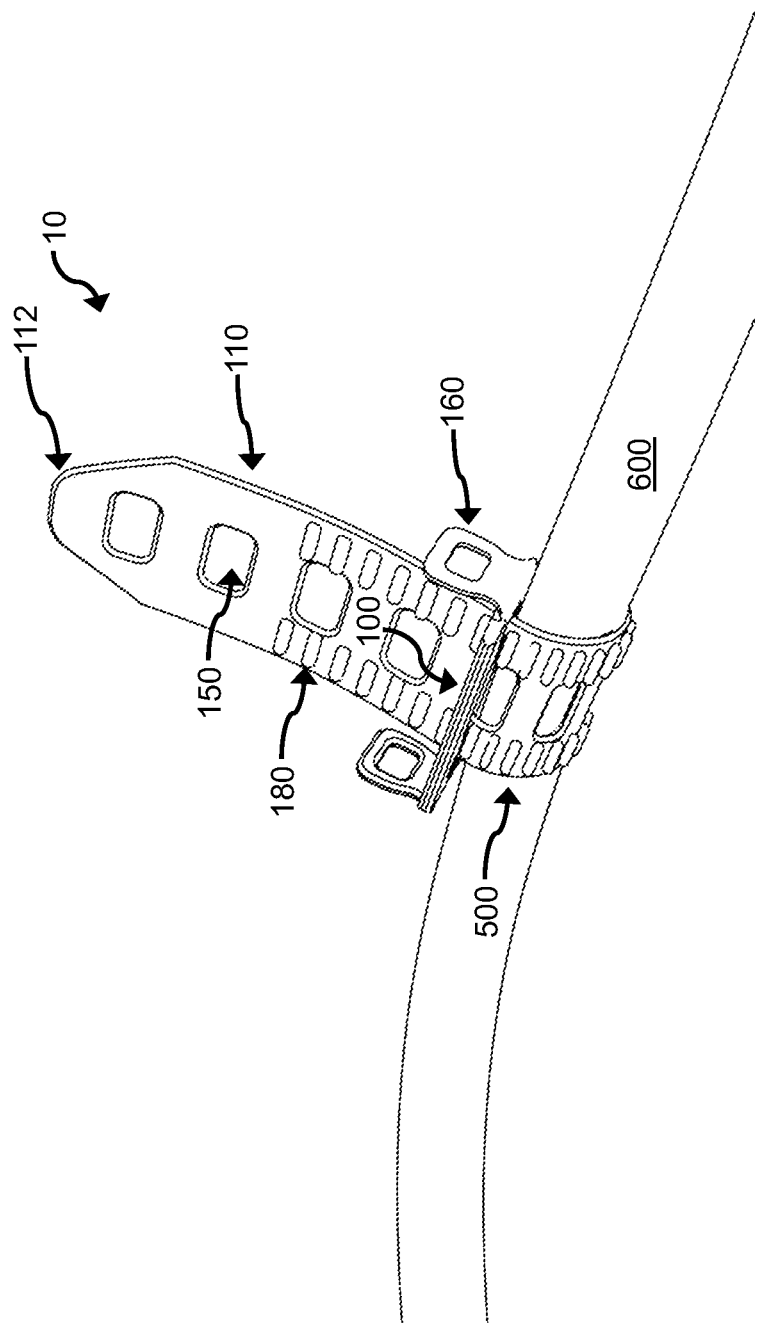
FIG. 6 is a perspective view of the device illustrated in FIG. 1 in a second or engaged state while securing a medical tube.
Figure 7:
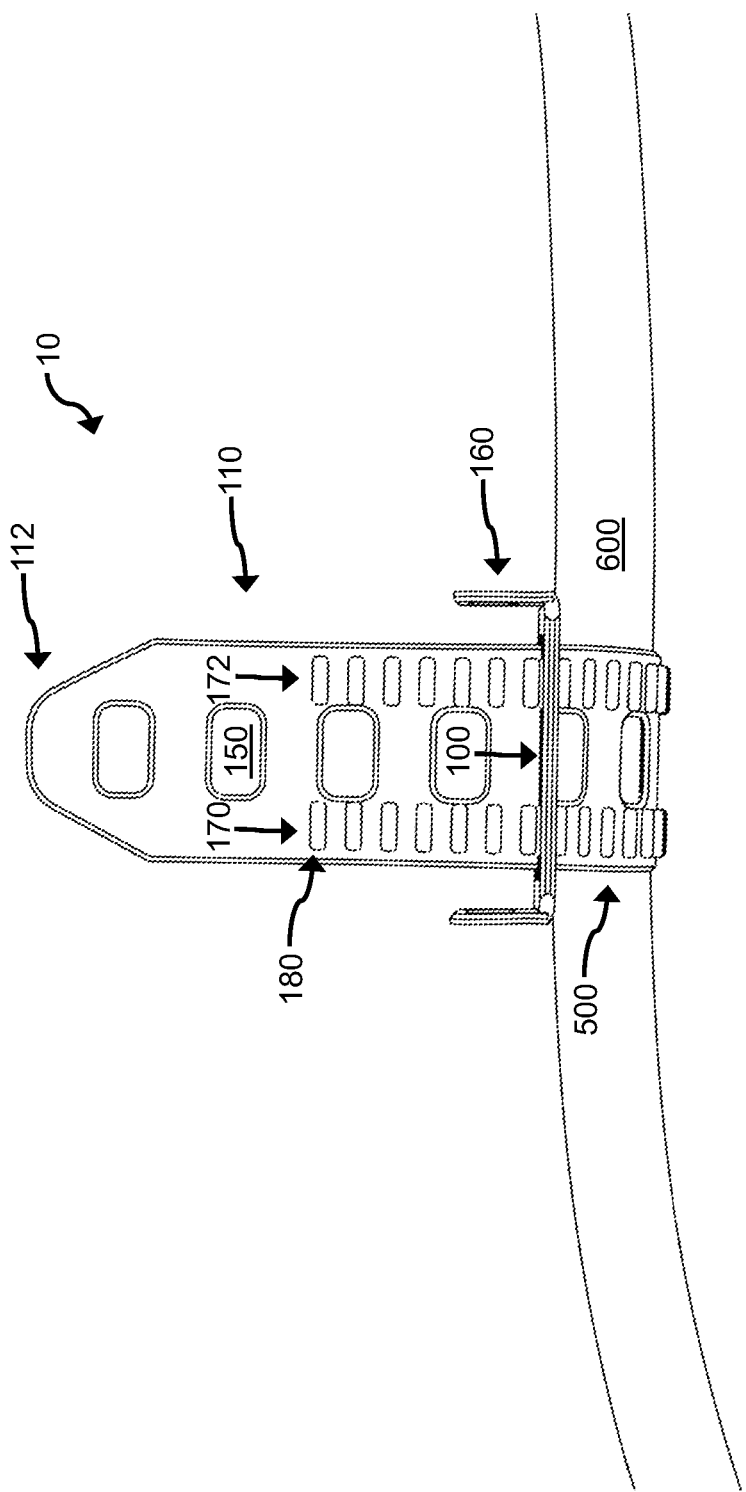
FIG. 7 is a front view of the device in a second or engaged state while securing the medical tube.

FIG. 6 is a perspective view of the device 10 in a second or engaged state while securing a medical tube 600. The medical tube 600 can be an intubation tube, thoracostomy tube or other medical tube. In some embodiments, the medical tube 600 has a diameter of about 6 mm to about 15 mm, including about 32 French. FIG. 7 is a front view of the device 10 in a second or engaged state while securing the medical tube 600.

Figure 8:
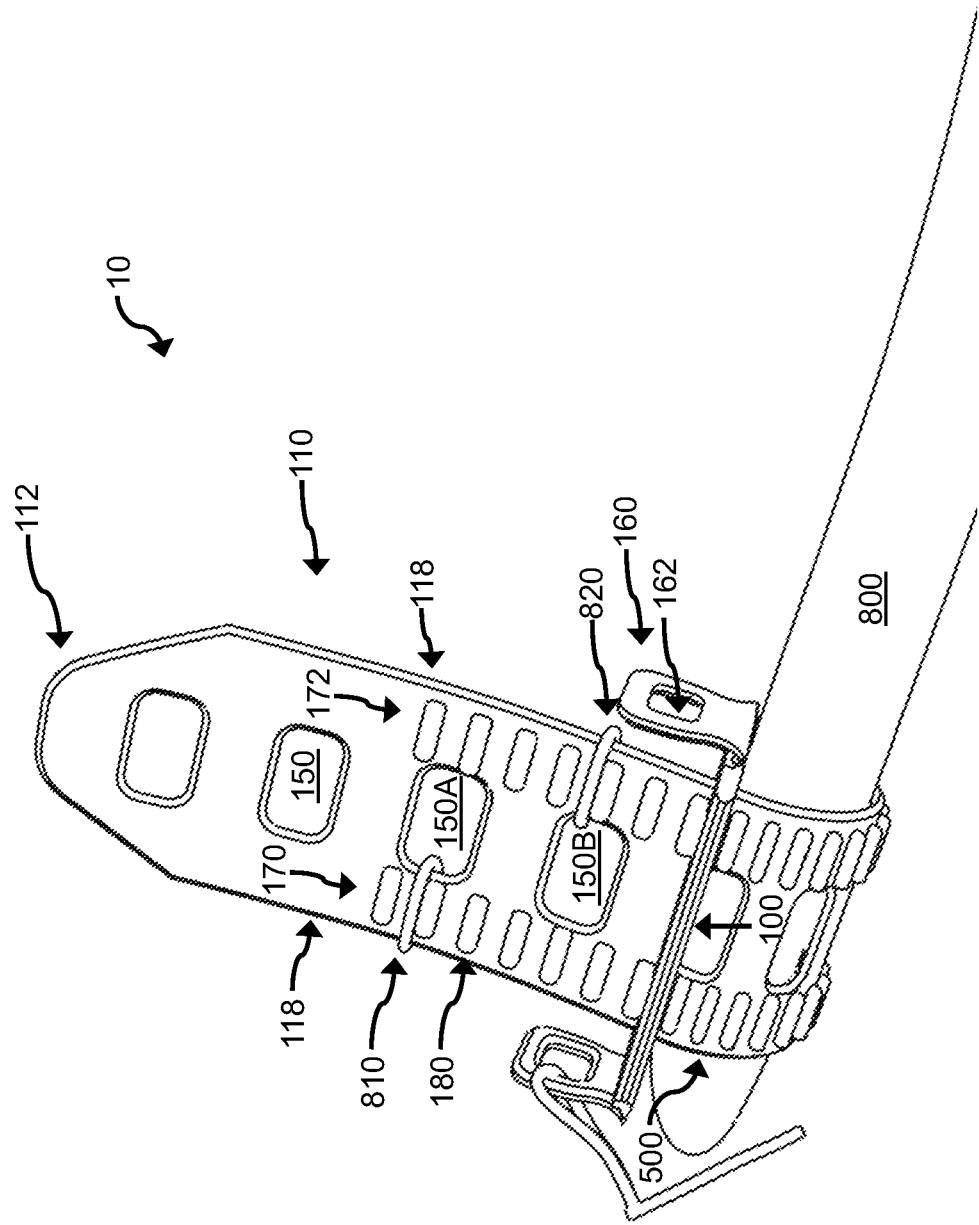
FIG. 8 is a perspective view of the device in a second or engaged state while securing an object.

FIG. 8 is a perspective view of the device 10 in a second or engaged state while securing an object 800. The object 800 can be the same as medical tube 600 or it can be another object. FIG. 8 also illustrates representative surgical thread loops 810, 820, 830 that are attached to the device 10.

A first surgical thread loop 810 is formed on the tail 110 between center hole 150A and a first side 118 of the tail 110. The first surgical thread loop 810 extends across the first row 170 of tail teeth 180. A second surgical thread loop 820 is formed on the tail 110 between center hole 150B and a second side 118 of the tail 110. The second surgical thread loop 820 extends across the second row 172 of tail teeth 180. In other embodiments, the first and second surgical thread loops 810, 820 can be formed using the same center hole 150 (e.g., center hole 150A). In addition, the first and second surgical thread loops 810, 820 can be formed using center holes 150 that are not adjacent to one another. Additional or fewer surgical thread loops (or other attachment mechanisms) can be attached to the tail 110.

The first and second surgical thread loops 810, 820 are preferably used to secure the device 10 to a patient undergoing a medical procedure such as a thoracotomy. For example, the first and second surgical thread loops 810, 820 can be attached to an article of clothing worn by the patient and/or to the patient itself. For example, surgical thread from one or both of the surgical thread loops 810, 820 can extend to and pass through the patient's skin. Alternatively, one or both of the first and second surgical thread loops 810, 820 can be used to secure the device 10 to object 800 (e.g., medical tube 600) or to another object.

A third surgical thread loop 830 is formed around a first ear 160 on the receiver 100. A portion of the third surgical thread loop 830 passes through the first ear aperture 162. In another embodiment, the third surgical thread loop 830 can be formed around a second ear 160 on the receiver 100. Alternative, a fourth surgical thread loop can be formed around the second ear 160 such that a surgical thread loop is formed around each ear 160.

The third surgical thread loop 830 and optional fourth surgical thread loop is/are preferably used to secure the device 10 to object 800 (e.g., medical tube 600) or to another object. Alternative, the third surgical thread loop 830 and optional fourth surgical thread loop can be used to secure the device 10 to a patient undergoing a medical procedure such as a thoracotomy. For example, the third surgical thread loop 830 and optional fourth surgical thread loop can be attached to an article of clothing worn by the patient and/or to the patient itself. For example, surgical thread from one or both of the third surgical thread loop 830 and optional fourth surgical thread loop can extend to and pass through the patient's skin.

In an example method of using the device 10, a physician can secure the device to a medical tube at a location that corresponds to a pre-measured length or depth of medical tube to inserted into the patient. For example, if the physician knows that the medical tube will need to be inserted about 16 cm into the patient's chest, the physician can secure the device 10 to the medical tube about 16 cm from its insertable end. The physician can then place the medical tube with the device 10 in a sterile location while the physician (or another physician) performs surgery or other procedure on the patient. At the appropriate time, the physician can then insert the medical tube into the patient's chest cavity. Since the device 10 is already attached to the medical tube, the device 10 will prevent the medical tube from being over-inserted into the patient's chest cavity. In addition, the device 10 can function as a marker for the pre-measured length or depth of the tube (e.g., about 16 cm or other length/depth). Next, the physician can secure the device 10 to the patient using the adhesive on the device 10. After securing the device 10 to the patient using adhesive on the device 10, the physician can optionally further secure the device 10 to the patient using surgical thread.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature, or element, of any or all the claims.

Many modifications and variations of the present invention are possible in light of the above teachings, and could be apparent for those skilled in the art. The scope of the invention is defined by the appended claims.

What is claimed is:

1. A device comprising:
   a receiver having a receiver body that defines a receiver aperture having a receiver aperture length that is measured with respect to a central axis of the device, the receiver body having a receiver tooth that extends into the receiver aperture to define a receiver tooth aperture having a receiver tooth aperture length that is measured with respect to the central axis, the receiver tooth aperture length narrower than the receiver aperture length; and
   a tail extending from the receiver along the central axis to a tail end, the tail defining a plurality of center holes and a plurality of tail teeth, the tail teeth axially aligned with the receiver tooth;
   wherein:
      the device is releasably configurable between a disengaged state and an engaged state,
      in the engaged state, the tail end is passed through the receiver aperture such that the tail forms a loop to secure an object, and the receiver tooth mechanically engages a first tail tooth to releasably secure the tail in the loop, and
      in the disengaged state, the receiver tooth and one of the tail teeth are mechanically disengaged and the tail end is removed from the receiver aperture; and
      wherein the receiver tooth comprises a first receiver tooth that defines a first receiver tooth aperture having a first receiver tooth aperture length, and the receiver body has a second receiver tooth that extends into the receiver aperture to define a second receiver tooth aperture having a second receiver tooth aperture length.

2. The device of claim 1, wherein the tail teeth form a row that is axially aligned with the receiver tooth.

3. The device of claim 2, wherein the tail teeth are evenly spaced along a length of the tail, the length of the tail measured with respect to the central axis.

4. The device of claim 1, wherein the center holes form a row that is axially aligned with the receiver aperture where the receiver aperture has the receiver aperture length.

5. The device of claim 4, wherein the center holes are evenly spaced along a length of the tail, the length of the tail measured with respect to the central axis.

6. The device of claim 4, wherein the center holes form a first row and the tail teeth form a second row, the first and second rows parallel to the central axis.

7. The device of claim 1, wherein the first receiver tooth aperture length is about the same as the second receiver tooth aperture length.

8. The device of claim 1, wherein the receiver aperture has the receiver aperture length in a middle region of the receiver aperture, and the first and second receiver teeth are disposed on opposing sides of the middle region of the receiver aperture.

9. The device of claim 1, further comprising an ear attached to the receiver, the ear having an ear body that defines an ear aperture.

10. The device of claim 1, wherein the center holes are configured to receive surgical thread.

11. The device of claim 1, wherein in the engaged state a diameter of the loop can be increased by mechanically engaging the receiver tooth with a second tail tooth, the second tail tooth disposed closer to the tail end than the first tail tooth.

12. The device of claim 1, wherein in the engaged state a diameter of the loop can be decreased by mechanically engaging the receiver tooth with a second tail tooth, the first tail tooth disposed closer to the tail end than the second tail tooth.

13. The device of claim 1, wherein in the engaged stated the loop is configured to secure a medical tube.

14. A device comprising:
   a receiver having a receiver body that defines a receiver aperture having a receiver aperture length that is measured with respect to a central axis of the device, the receiver body having a receiver tooth that extends into the receiver aperture to define a receiver tooth aperture having a receiver tooth aperture length that is measured with respect to the central axis, the receiver tooth aperture length narrower than the receiver aperture length;
   a tail extending from the receiver along the central axis to a tail end, the tail defining a plurality of center holes and a plurality of tail teeth, the tail teeth axially aligned with the receiver tooth; and
   an ear attached to the receiver, the ear having an ear body that defines an ear aperture;
   wherein:
      the device is releasably configurable between a disengaged state and an engaged state,
      in the engaged state, the tail end is passed through the receiver aperture such that the tail forms a loop to secure an object, and the receiver tooth mechanically engages a first tail tooth to releasably secure the tail in the loop, and
      in the disengaged state, the receiver tooth and the one of the tail teeth are mechanically disengaged and the tail end is removed from the receiver aperture; and wherein the ear is laterally offset from the central axis along a lateral axis, the lateral axis orthogonal to the central axis.

15. A device comprising:

a receiver having a receiver body that defines a receiver aperture having a receiver aperture length that is measured with respect to a central axis of the device, the receiver body having a receiver tooth that extends into the receiver aperture to define a receiver tooth aperture having a receiver tooth aperture length that is measured with respect to the central axis, the receiver tooth aperture length narrower than the receiver aperture length;

a tail extending from the receiver along the central axis to a tail end, the tail defining a plurality of center holes and a plurality of tail teeth, the tail teeth axially aligned with the receiver tooth; and an ear attached to the receiver, the ear having an ear body that defines an ear aperture;

wherein:
   the device is releasably configurable between a disengaged state and an engaged state,
   in the engaged state, the tail end is passed through the receiver aperture such that the tail forms a loop to secure an object, and the receiver tooth mechanically engages a first tail tooth to releasably secure the tail in the loop, and
   in the disengaged state, the receiver tooth and the one of the tail teeth are mechanically disengaged and the tail end is removed from the receiver aperture; and
wherein the ear comprises a first ear that has a first ear body that defines a first ear aperture, and the device further comprises a second ear having a second ear body that defines a second ear aperture.

16. The device of claim 15, wherein the first and second ears are laterally offset from the central axis along a lateral axis, the lateral axis orthogonal to the central axis.

17. The device of claim 16, wherein the first and second ears are attached to opposing sides of the receiver.

18. The device of claim 17, wherein the first and second ears are foldably attached to the opposing sides of the receiver.

19. A device comprising:

a receiver having a receiver body that defines a receiver aperture having a receiver aperture length that is measured with respect to a central axis of the device, the receiver body having a receiver tooth that extends into the receiver aperture to define a receiver tooth aperture having a receiver tooth aperture length that is measured with respect to the central axis, the receiver tooth aperture length narrower than the receiver aperture length; and a tail extending from the receiver along the central axis to a tail end, the tail defining a plurality of center holes and a plurality of tail teeth, the tail teeth axially aligned with the receiver tooth;

wherein:
   the device is releasably configurable between a disengaged state and an engaged state,
   in the engaged state, the tail end is passed through the receiver aperture such that the tail forms a loop to secure an object, and the receiver tooth mechanically engages a first tail tooth to releasably secure the tail in the loop, and
   in the disengaged state, the receiver tooth and the one of the tail teeth are mechanically disengaged and the tail end is removed from the receiver aperture; and
wherein the receiver and the tail comprise a monolithic structure.

20. A device comprising:

a receiver having a receiver body that defines a receiver aperture having a receiver aperture length that is measured with respect to a central axis of the device, the receiver body having a receiver tooth that extends into the receiver aperture to define a receiver tooth aperture having a receiver tooth aperture length that is measured with respect to the central axis, the receiver tooth aperture length narrower than the receiver aperture length;

a tail extending from the receiver along the central axis to a tail end, the tail defining a plurality of center holes and a plurality of tail teeth, the tail teeth axially aligned with the receiver tooth; and an adhesive disposed on the tail;

wherein:
   the device is releasably configurable between a disengaged state and an engaged state,
   in the engaged state, the tail end is passed through the receiver aperture such that the tail forms a loop to secure an object, and the receiver tooth mechanically engages a first tail tooth to releasably secure the tail in the loop, and
   in the disengaged state, the receiver tooth and the one of the tail teeth are mechanically disengaged and the tail end is removed from the receiver aperture.

* * * * *